US006632203B2

(12) United States Patent
Swisher et al.

(10) Patent No.: US 6,632,203 B2
(45) Date of Patent: Oct. 14, 2003

(54) SAMPLING PORT FOR A DRAINAGE DEVICE

(75) Inventors: David Rork Swisher, St. Charles, MO (US); Jacky Yam, St. Louis, MO (US)

(73) Assignee: Sherwood Services AG, Schaffausen (CH)

( * ) Notice: Subject to any disclaimer, the term of this patent is extended or adjusted under 35 U.S.C. 154(b) by 38 days.

(21) Appl. No.: 09/862,076

(22) Filed: May 21, 2001

(65) Prior Publication Data

US 2002/0173757 A1 Nov. 21, 2002

(51) Int. Cl.[7] .................................................. A61M 1/00
(52) U.S. Cl. ........................................ 604/317; 604/320
(58) Field of Search ................................. 604/320, 317

(56) References Cited

U.S. PATENT DOCUMENTS

| 3,363,626 | A |   | 1/1968  | Bidwell et al. ............ 128/276 |
| 4,767,417 | A |   | 8/1988  | Boehringer et al. ......... 604/31 |
| 4,988,342 | A |   | 1/1991  | Herweck et al. |
| 5,114,416 | A | * | 5/1992  | Karwoski et al. ........... 604/317 |
| 5,141,504 | A |   | 8/1992  | Herweck et al. |
| 5,154,712 | A |   | 10/1992 | Herweck et al. |
| 5,184,652 | A |   | 2/1993  | Fan ............................. 141/21 |
| 5,275,584 | A |   | 1/1994  | Hogan |
| 5,279,600 | A |   | 1/1994  | Hogan |
| 5,286,262 | A |   | 2/1994  | Herweck et al. |
| 5,397,299 | A |   | 3/1995  | Karwoski et al. |
| 5,401,262 | A |   | 3/1995  | Karwoski et al. |
| 5,584,808 | A |   | 12/1996 | Healy |
| 5,697,900 | A |   | 12/1997 | Peluso et al. |
| 5,743,894 | A | * | 4/1998  | Swisher ...................... 604/319 |
| 5,925,025 | A |   | 7/1999  | Weilbacher et al. |
| 6,146,374 | A | * | 11/2000 | Erskine et al. .............. 604/533 |

* cited by examiner

*Primary Examiner*—Timothy L. Maust
*Assistant Examiner*—Filip Zec
(74) *Attorney, Agent, or Firm*—Ari M. Bai; Greensfelder, Hemker & Gale, P.C.

(57) ABSTRACT

A sampling port having a mechanical valve for a drainage apparatus is disclosed which permits a practitioner to directly access a collection chamber of the drainage apparatus using a needle-less syringe for withdrawing a sample of fluid therefrom. The sampling port comprises a port in direct communication with the collection chamber and a mechanical valve partially disposed inside the port. The mechanical valve comprises a generally tubular body containing a spring loaded valve that is normally closed to fluid flow communication and operable using a needle-less tip syringe to actuate the valve. In operation, a practitioner engages the needle-less tip syringe to the valve which places the valve in an open position and permits fluid flow into the syringe as the practitioner draws back on the plunger of the syringe.

22 Claims, 6 Drawing Sheets

SAMPLING PORT FOR A DRAINAGE DEVICE

BACKGROUND OF THE INVENTION

1. Field of the Invention

The present invention relates to a chest drainage system, and particularly to a chest drainage device for suctioning gases and liquids from the chest cavity of a patient. More specifically, the present invention relates to a sampling port for directly accessing a collection chamber of the chest drainage device.

2. Prior Art

A chest drainage device is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various respiratory infections can cause build up of liquid and gases around the lungs in the intrapleural space. When this happens, it causes the lungs to collapse to a volume much less than that of the pleural cavity, thereby severely impairing the breathing functions of the patient. The lungs can be re-expanded to their normal state to fill the pleural cavity by draining the liquid and gases from the pleural cavity using a chest drainage device.

There are many kinds of chest drainage devices used to drain the pleural cavity of a patient. One kind of drainage device, sometimes referred to as a "three-bottle" type, is illustrated in U.S. Pat. No. 3,363,626 to Bidwell et al. entitled "Underwater Drainage Apparatus". The "three-bottle" type drainage device has three interconnecting chambers which comprise: (1) a collection chamber for collecting liquids and gases suctioned from the patient's pleural cavity through a catheter; (2) an underwater seal chamber which communicates with the collection chamber and has a water seal which acts as a one way valve for passing gases collected from the patient's pleural cavity to the atmosphere; and (3) a suction control chamber for limiting the maximum suction (or negative pressure) applied to the patient's pleural cavity.

In operation, a source of vacuum is applied to the Bidwell et al. device such that the negative pressure generated in the collection chamber causes shed liquid and gases from the patient's pleural cavity to collect inside the collection chamber. As the liquid and gases enter the collection chamber, the vacuum establishes a fluid pathway which causes the collected gases to pass from the collection chamber and through the water seal of the water seal chamber. Once through the water seal, the gases are evacuated from the drainage device through a vacuum port which is in communication with the water seal chamber.

Often it is desirable to draw a sample of collected fluid directly from the collection chamber of a chest drainage device in order to perform periodic testing of the fluid. The chest drainage devices of the prior art use non-mechanical valves which require a needle tipped syringe in order to directly access fluid in the collection chamber. These non-mechanical valves are usually grommet or rubber bung ports located adjacent the collection chamber which have an elastomeric membrane that reseals when penetrated by a needle tipped syringe. However, the drawback with using a needle tipped syringe with such prior art sampling ports is the potential danger of a user being inadvertently stuck with a contaminated needle after withdrawing a sample of fluid from the collection chamber.

Therefore, there is a need in the art for a sampling port which permits direct withdraw of a fluid sample from the collection chamber of a drainage device using a needle-less syringe. There is a further need in the art for a drainage device having a mechanical sampling port that permits easy and direct access to the collection chamber.

OBJECTS AND SUMMARY OF THE INVENTION

The primary object of the present invention is to provide a mechanical sampling port for a drainage device.

Another object of the present invention is to provide a mechanical sampling port which directly communicates with the collection chamber of a medical drainage device using a needle-less syringe.

In brief summary, the present invention overcomes and substantially alleviates the deficiencies present in the art by providing a mechanical sampling port for a drainage device which allows direct access to the collection chamber using a needle-less syringe.

Preferably, the drainage device comprises a mechanical sampling port and related method of use thereof for a chest drainage device that permits the practitioner to withdraw a sample of fluid directly from the collection chamber using a needle-less syringe. The sampling port comprises a mechanical two way valve which directly communicates and accesses the collection chamber. The practitioner utilizes the sampling port by engaging a needle-less syringe, for example a luer tip syringe, into the two way valve inside the sampling port which places the two-way valve in the open position. When the practitioner desires to withdraw a sample of fluid, he or she simply pulls back the plunger of the syringe until a sufficient amount of blood or fluid from the collection chamber fills the syringe. Once a sufficient amount of fluid is withdrawn from the collection chamber, the user disengages the syringe which automatically returns the two-way valve to the normally closed position.

In an alternate embodiment, the sampling port uses a one-way valve instead of a two-way valve to access the collection chamber. The one-way valve comprises a body having a first interior chamber in communication with a second interior chamber separated by an inner shoulder. Similar to the preferred embodiment, an insert is engaged to one end of the body. However, unlike the preferred embodiment, the alternate embodiment includes a spring-loaded valve member which selectively engages a seat formed by the insert when the one-way valve is operated between open and closed positions. In operation, the practitioner engages a needle-less syringe to one end of the one-way valve and actuates the plunger of the syringe to create a suction inside first and second interior chambers. The suction causes the spring-loaded valve member to disengage from the seat and permit fluid flow communication with the collection chamber so that a sample may be withdrawn.

These and other objects of the present invention are realized in the preferred embodiment, described by way of example and not by way of limitation, which provides for a mechanical sampling port for a drainage device that permits the practitioner to use a needle-less syringe to directly access the collection chamber.

Additional objects, advantages and novel features of the invention will be set forth in the description which follows, and will become apparent to those skilled in the art upon

DETAILED DESCRIPTION OF THE INVENTION

Figure 1:
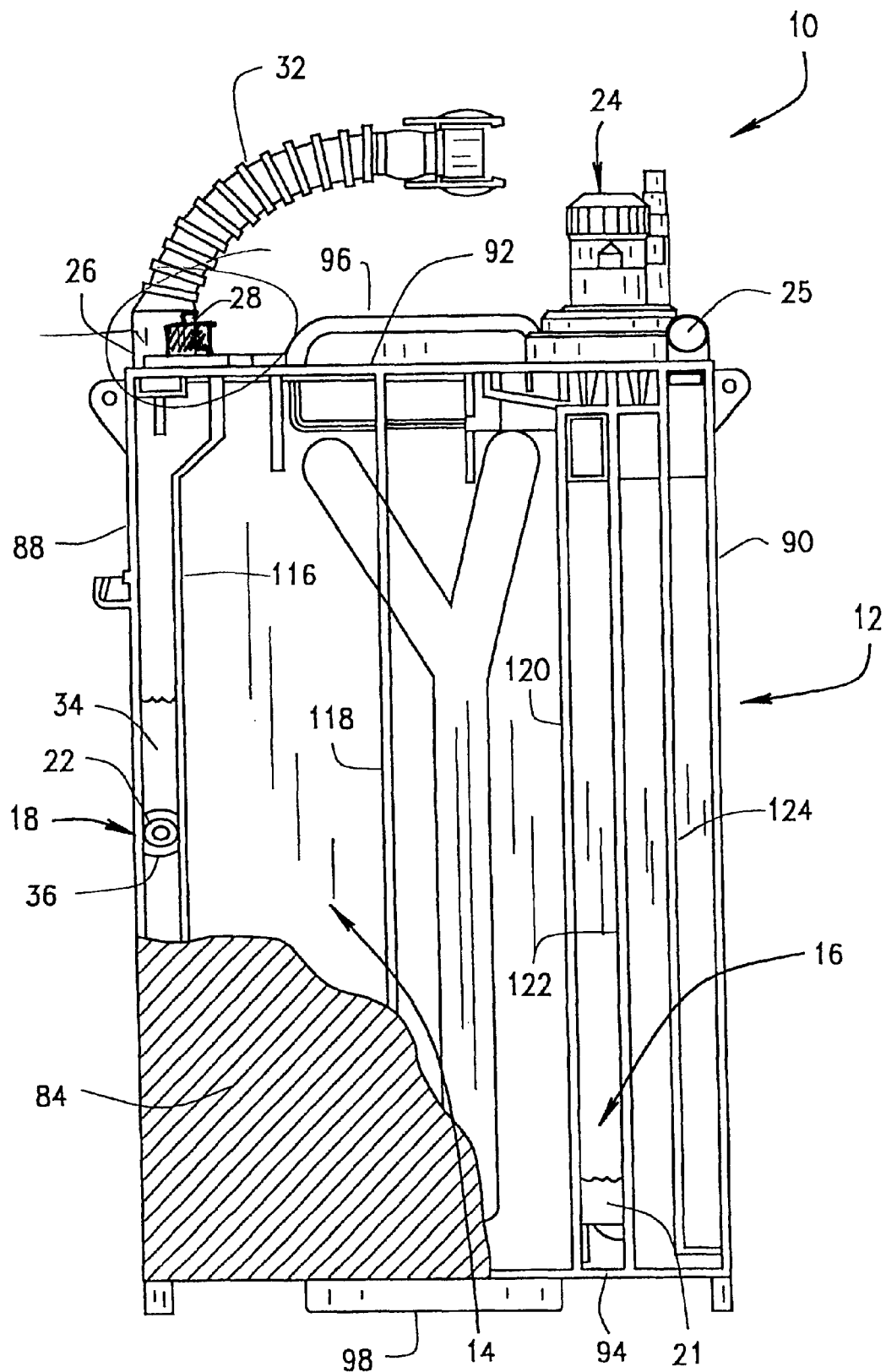
FIG. 1 is a front view of the drainage device according to the present invention.
Figure 2:
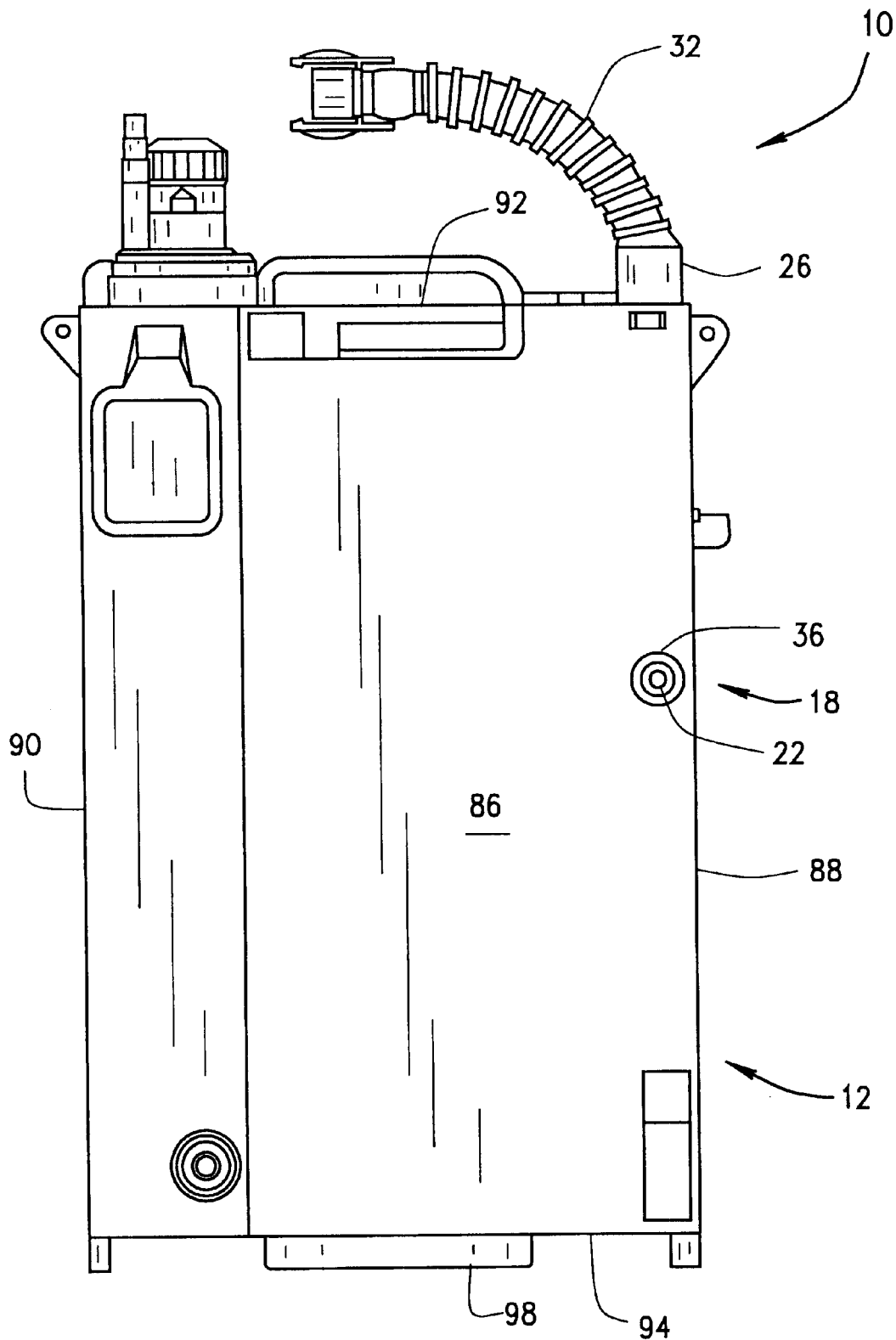
FIG. 2 is a rear view of the drainage device showing the sampling port according to the present invention.

Referring to the drawings, the preferred embodiment of the drainage device used with the sampling port 18 of the present invention is illustrated and generally indicated as 10 in FIG. 1. Drainage device 10 comprises a casing 12 defined by a front wall 84, rear wall 86 (FIG. 2), top wall 92, bottom wall 94, and opposing side walls 88 and 90. Casing 12 is further defined by a collection chamber 14 for the collection of shed fluids from a patient's pleural cavity, a water seal chamber 16 in communication with the collection chamber 14 for preventing reflux of evacuated gases back to the patient, and a suction control chamber 17 (FIG. 4) in communication with the water seal chamber 16 for regulating the degree of vacuum inside drainage device 10. As further shown, casing 12 comprises interior partitions 116, 118, 120, 122 and 124 which are parallel to front and rear walls 84 and 86, and a partition 125 (FIG. 4), which is parallel to front and rear walls 84 and 86, that divide the interior of casing 12 into collection chamber 14, water seal chamber 16 suction control chamber 17 as well as a number of other various chambers and compartments.

Figures 3, 4:
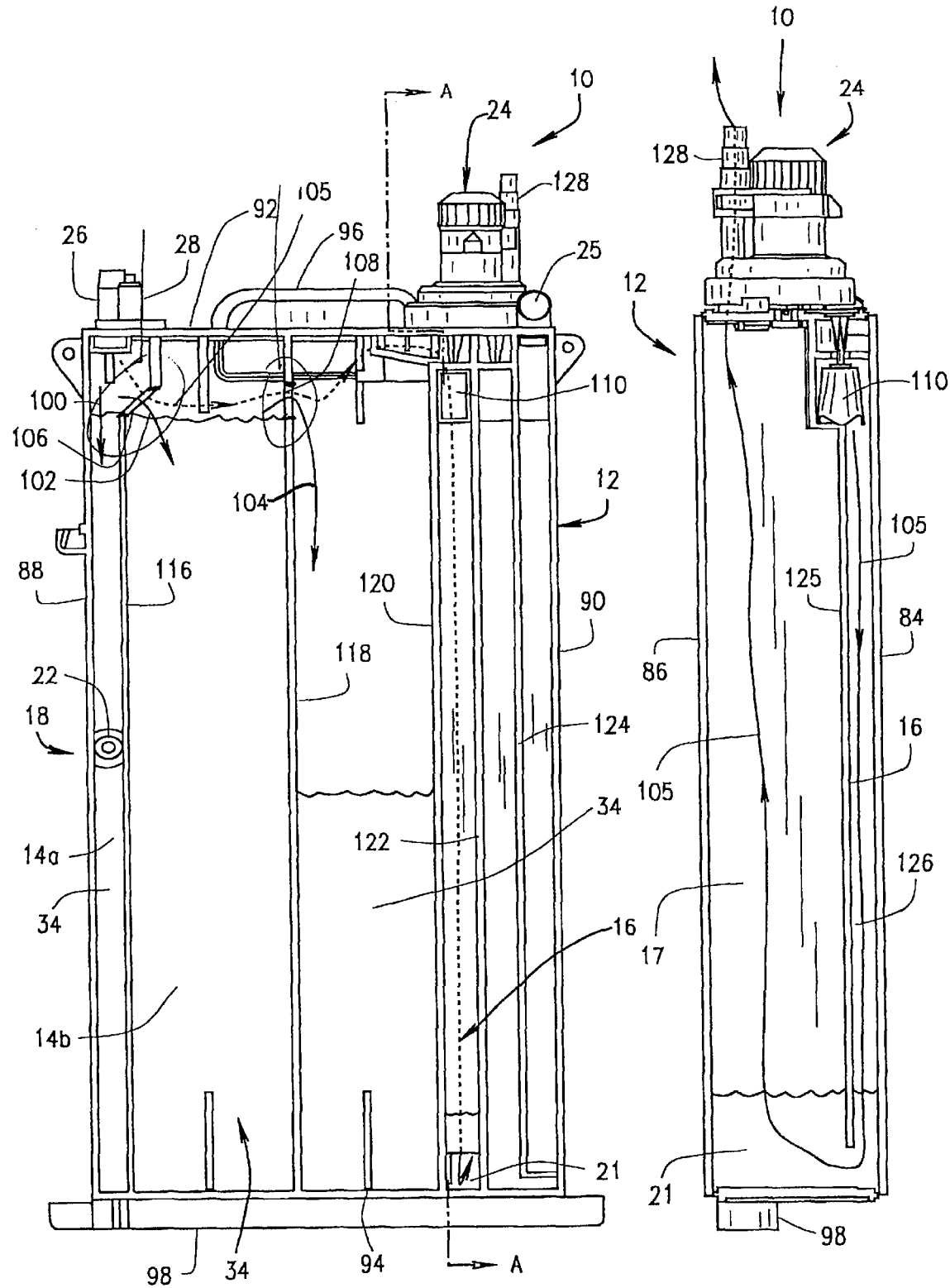
FIG. 3 is a front view of the drainage device illustrating its basic operative features, functions and air flow pathways.
FIG. 4 is a cross-sectional view along line A—A of FIG. 3 according to the present invention.

Referring to FIG. 3, drainage device 10 comprises a negative pressure relief valve 28 for venting excess negative pressure from within casing 12, a collection port 26 for attachment to patient tubing 32 (FIG. 1), a vacuum regulator assembly 24 for the mechanical regulation of vacuum inside drainage device 10, and a vacuum indicator assembly 25 for giving a visual indication to the user of proper vacuum being applied to collection chamber 14. In the alternative, the present invention contemplates that the sampling port 18 may be used with other kinds of drainage devices 10, for example a drainage device 10 having a water column to regulate the level of vacuum rather than a vacuum regulator assembly 24. A handle 96 is also provided along top wall 92 for handling and transporting drainage device 10, while a rotatable stand 98 is attached to bottom wall 94 for providing a stable platform for drainage device 10.

As further shown, partitions 116 and 118 divide collection chamber 14 into compartments 14a, 14b and 14c, to facilitate periodic monitoring of the level of liquid 34 collected from the patient's chest cavity. As shown by arrow 100, vacuum applied to drainage device 10 forces blood and other liquid 34 from the patient's chest cavity into compartment 14a through collection port 26 via patient tubing 32. When compartment 14a is filled to capacity, arrow 102 illustrates that any additional liquid 34 will overflow through a port 106 and into compartment 14b until that compartment is completely filled. Once compartment 14b is filled to capacity, arrow 104 shows that any additional liquid 34 will overflow through a port 108 and drop into compartment 14c. The present invention contemplates the use of appropriate indicia (not shown) marked along front wall 84 (FIG. 1) for each compartment 14a, 14b and 14c, respectively, for providing a clear visual indication of the level of liquid 34 in each respective compartment.

Referring to FIGS. 3 and 4, once fluid from the patient's cavity is deposited inside collection chamber 14, gases are evacuated through the water seal chamber 16 as illustrated by arrow 105. Water seal chamber 16 prevents reflux of gases back to the patient by preventing reentry of such gases into the collection chamber 14 using a buoyant valve 110 in combination with a water seal 21. The structure and operation of the buoyant valve 110 is disclosed in U.S. Pat. No. 5,931,821 to Weilbacher et al., entitled "Chest Drainage Unit With Controlled Automatic Excess Negativity Relief Feature" which is incorporated by reference in its entirety. The water seal chamber 16 comprises a compartment 126 having upper and lower portions with the upper portion housing valve 110 and the lower portion having water seal 21 disposed therein. The lower portion of compartment 126 communicates with the lower portion of the suction control chamber 17 which is separated from compartment 126 by partition 125. As gases pass through the water seal 21 from collection chamber 14, the gases are evacuated from drainage device 10 through vacuum regulator assembly 24 to a vacuum source (not shown).

As further shown, vacuum regulator assembly 24 provides a means for regulating the degree of vacuum, venting of excess positive pressure, and a pathway for evacuating gases from drainage device 10. The basic operation of vacuum regulator assembly 24 is disclosed in U.S. Pat. No. 4,911,697 to Kerwin and is herein incorporated by reference in its entirety. Preferably, vacuum regulator assembly 24 comprises a positive pressure relief valve (not shown) for venting excess positive pressure generated inside collection port 14 and a vacuum port 128 for communicating with a source of vacuum. Both the positive pressure relief valve and vacuum port 128 communicate with suction control chamber 17 which is in fluid flow communication with water seal 21. Once the gas passes through water seal 21 it is evacuated from the suction control chamber 17 through the vacuum port 128 to the vacuum source.

Figures 5, 6:
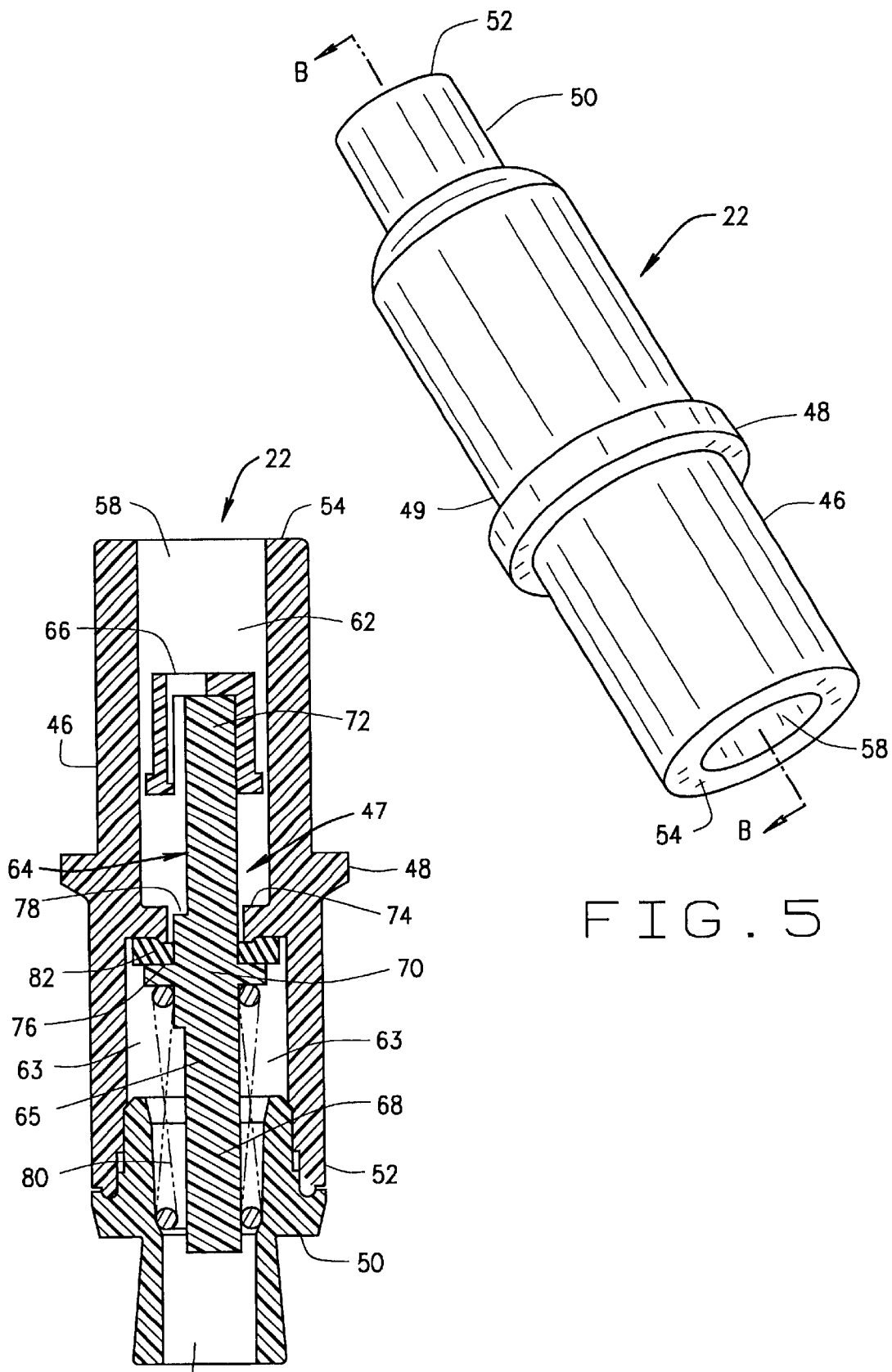
FIG. 5 is a perspective view of the two way valve of the sampling port according to the present invention.
FIG. 6 is a cross-sectional view of the two way valve taken along line B—B of FIG. 5 according to the present invention.
Figure 8:
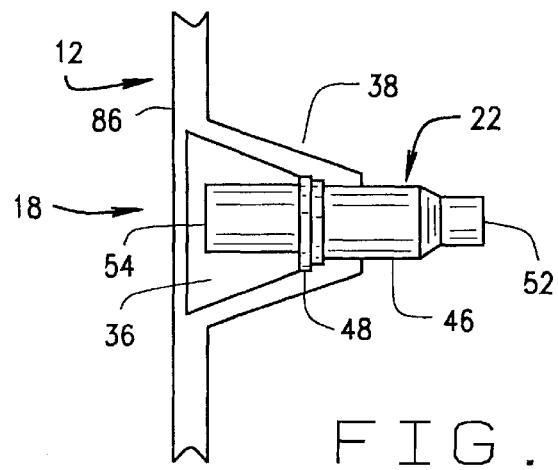
FIG. 8 is a partial cross-sectional view of the two way valve disposed inside the sampling port according to the present invention.

Referring to FIGS. 1–3 and 8, sampling port 18 of the present invention shall now be discussed. Sampling port 18 is located along rear wall 86 of drainage device 10 such that port 18 communicates directly with collection chamber 14 along compartment 14a, although the present invention contemplates that port 18 may be located along any wall which communicates directly with collection chamber 14 for withdrawing a sample. As further shown, sampling port 18 comprises an aperture 36 formed through rear wall 86 having a two-way valve 22 disposed therein. Referring to FIG. 5, two-way valve 22 has a generally tubular shaped body 46 having a distal end 52 and proximal end 54 with an annular flange 48 formed around a middle portion 49 of body 46. Flange 48 serves to securely engage and retain two-way valve 22 within aperture 36, as shall be explained in greater detail below. Referring to FIGS. 5 and 6, two-way valve 22 further comprises an insert 50 extending axially from body 46 having an opening 60 which is securely coupled to the distal end 52 of two-way valve 22. The proximal end 54 of two-way valve 22 forms a proximal opening 58 which selectively communicates with distal opening 60 through a main chamber 47 when two-way valve 22 is placed in the open position. As illustrated in FIG. 8, rear wall 86 includes a retention portion 38 which extends inwardly from wall 86 and is sized and shaped to securely engage flange 48 such that the distal end 52 of two-way valve 22 is oriented to communicate directly with the collection chamber 14.

Referring specifically to FIG. 6, the basic operation of two-way valve 22 shall be discussed in greater detail. Two-way valve 22 is a spring loaded valve that is normally closed to fluid flow communication. As further shown, proximal opening 58 opens into a first interior chamber 62 formed within main chamber 47 where an activation member 66 is disposed therein and attached to a push rod 64. Push rod 64 has an elongated body 65 which includes a proximal portion 72 that is disposed in first interior chamber 62, a middle portion 70 that has an annular flange 76 for selectively sealing off fluid flow through body 46, and a distal portion 68 which is disposed within a second interior chamber 63. First interior chamber 62 and the second interior chamber 63 are separated by an inner shoulder 74 which defines an aperture 78 adapted to receive push rod 64 slidably therethrough. To maintain a fluid tight seal when two-way valve 22 is in the closed position, an annular seal 82 is provided which is coupled around push rod 64 adjacent flange 76 and is adapted to seal off aperture 78 from fluid flow communication between first interior chamber 62 and second interior chamber 63 when two-way valve 22 is placed in the normally closed position.

To bias two-way valve 22 in the normally closed position, a spring 80 is provided which has one end attached to the middle portion 70 of push rod 64 and the other end attached to insert 50 by means well known in the art. The spring 80 creates a continual forward bias towards the proximal end 54 such that seal 82 is forced to abut inner shoulder 74 and close off fluid flow communication between first and second interior chambers 62 and 63, unless push rod 64 is properly activated.

Figures 7A, 7B:
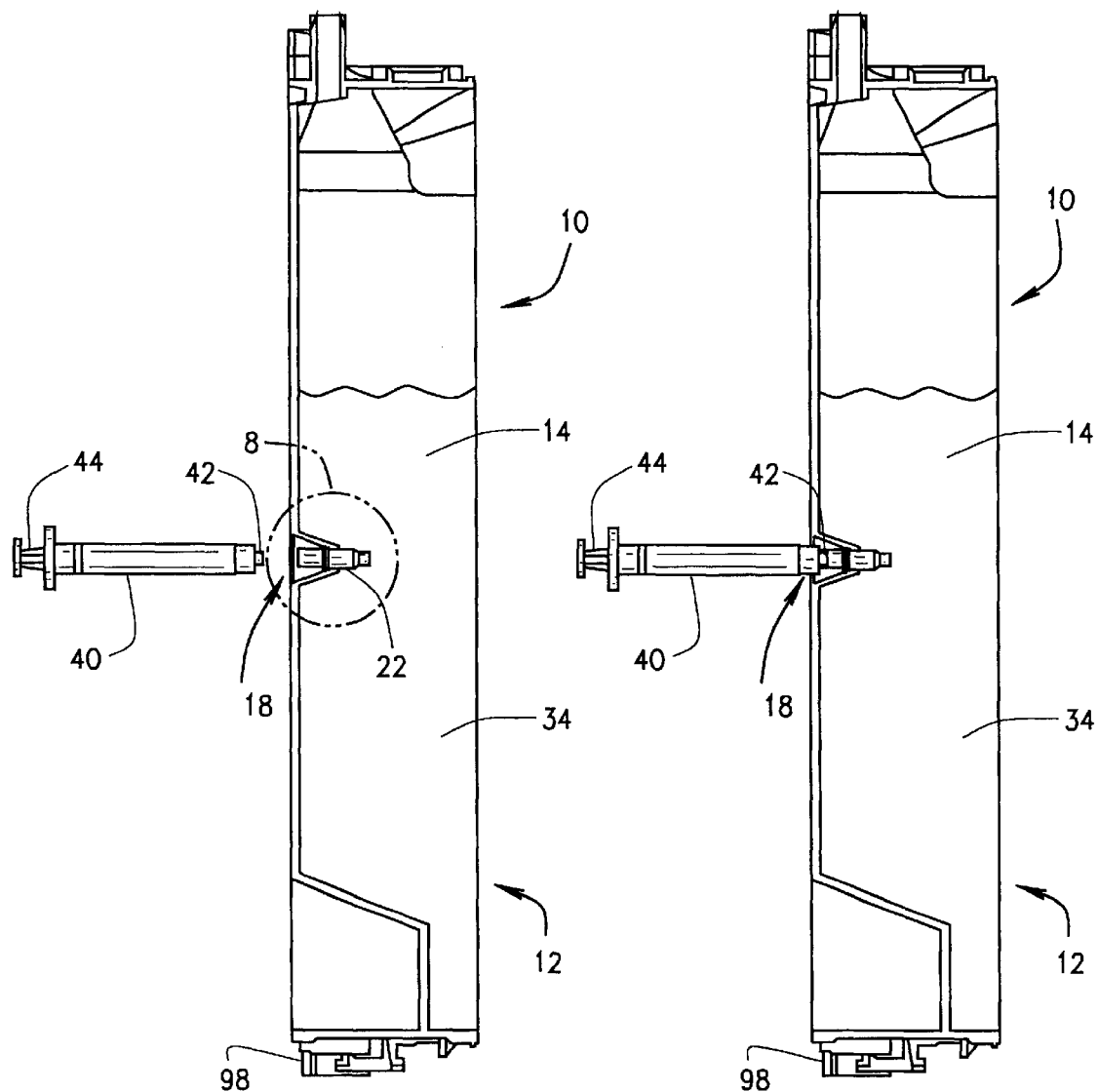
FIG. 7a is a partial cross-sectional view illustrating the method of engaging a needle-less syringe to the sampling port prior to engagement with the two way valve according to the present invention.
FIG. 7b is a partial cross-sectional view illustrating the method of engaging a needle-less syringe to the sampling port showing the needle-less syringe engaged with the two way valve according to the present invention.

In operation, two-way valve 22 is activated by the practitioner inserting a conventional needle-less syringe 40, preferably having a luer tip 42, through the proximal opening 58 until luer tip 42 engages activation member 66, as shown in the sequence illustrated in FIGS. 7a and 7b. As the practitioner pushes the syringe 40 through first interior chamber 62 and contacts activation member 66, the push rod 64 is caused to move axially towards distal end 52 which overcomes the spring force applied by spring 80 and unseats seal 82 from aperture 78, thereby establishing fluid flow communication between first and second interior chambers 62 and 63. The practitioner may then draw back the plunger 44 of syringe 40 so that a sample of liquid 34 may be taken directly from the collection chamber 14 and drawn into syringe 40. Once a predetermined amount of liquid 34 is withdrawn directly from collection chamber 14, the practitioner disengages the luer tip 42 from activation member 66 which causes the spring force applied by spring 80 to force seal 82 against aperture 78 and return two-way valve 22 to the normally closed position.

Figure 9A:
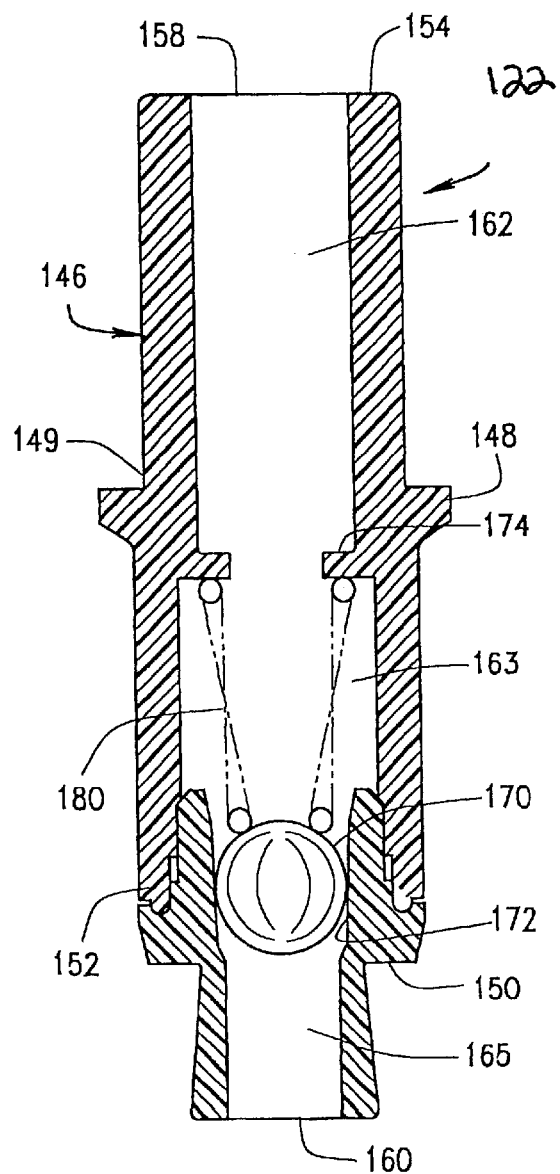
FIG. 9a is a cross-sectional view of an alternate embodiment of a one-way valve shown in a closed position according to the present invention.
Figure 9B:
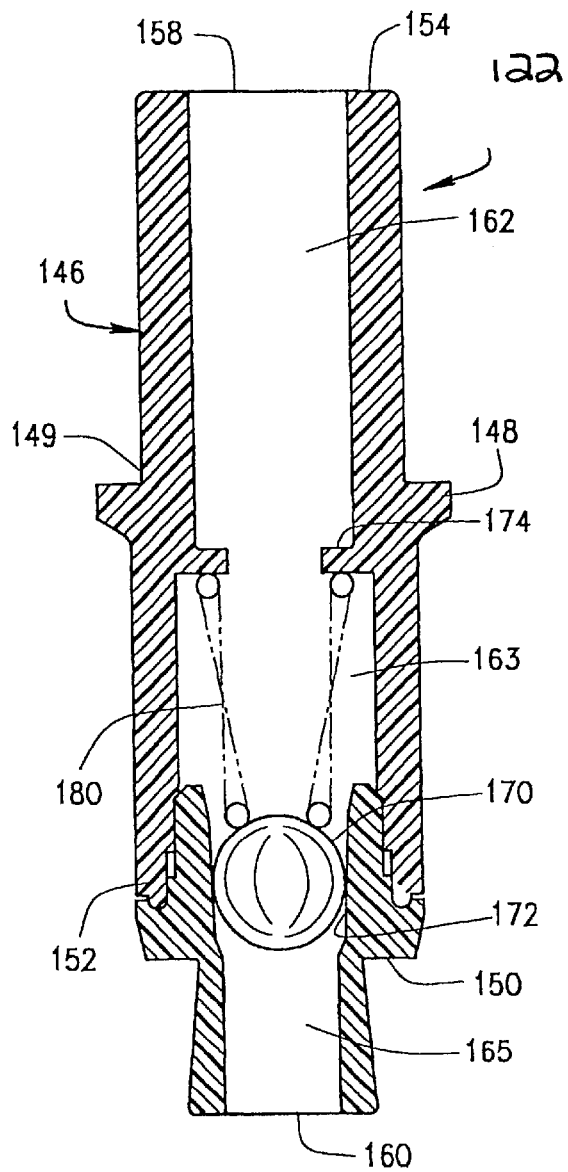
FIG. 9b is a cross-sectional view of the alternate embodiment of the one-way valve shown in the open position according to the present invention.

Referring to FIGS. 9a and 9b, an alternate embodiment of two way valve 22 will now be discussed. The present invention contemplates utilizing a one-way valve 122 rather than the two-way valve 22 of the preferred embodiment. One-way valve 122 is similar to the two-way valve 22 in that one-way valve 122 is a spring-loaded valve that is normally closed to fluid flow communication. As shown, one-way valve 122 comprises a tubular shaped body 146 having a distal end 152 and a proximal end 154 with an annular flange 148 formed around a middle portion 149. An insert 150 is securely engaged with the distal end 152 of tubular body 146. The proximal end 154 forms a proximal opening 158 which selectively communicates with a distal opening 152 through first and second interior chambers 162 and 163, while distal end 160 communicates with a third interior chamber 165. One-way valve 122 further includes a spring-loaded valve member 170 operatively connected to a spring 180. As further shown, spring 180 provides a spring force which maintains valve member 170 in a normally closed position against a seat 172 which prevents fluid flow communication between second interior chamber 163 and third interior chamber 165. One end of spring 180 is attached to an inner shoulder 174 and the other end to valve member 170 by means well known in the art. In operation, a practitioner engages the end of a luer-tip syringe (not shown) to the proximal end 154 of one-way valve 122 and pulls back on the plunger. As the plunger is pulled back, suction is created within the first and second interior chambers 162 and 163 that overcomes the applied spring force and automatically causes the valve member 170 to disengage from seat 172 to permit fluid flow through third interior chamber 165. Once a predetermined amount of fluid has been withdrawn from the collection chamber 14, the practitioner disengages the syringe from the one-way valve 122 which terminates the applied suction and causes valve member 170 to engage seat 172.

Although the present invention contemplates that syringe 40 have a luer tip 42, other suitable needle-less means of engaging two-way valve 22 may be utilized which are adapted to mechanically activate valve 22 in the manner described above.

Preferably, sampling port 18 is located along a mid-point between top and bottom walls 92 and 94 as illustrated in FIG. 1; however, sampling port 18 may also be located along any suitable point along casing 12 as long as port 18 communicates directly with collection chamber 14.

Preferably, two-way valve 22 is a BESPAK valve manufactured by Bespak of Cary, N.C., although any mechanical two way valve which is actuatable using a needle-less syringe is felt to fall with the spirit and scope of the present invention.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. In combination, a sampling port and a drainage apparatus for obtaining a liquid sample comprising:
   a drainage device having a casing, said casing defining a collection chamber for the collection of a liquid drained from a cavity of a patient, said casing further defining an aperture in communication with said collection chamber;
   a valve disposed in said aperture and in communication with said collection chamber, said valve being operable between a normally closed position wherein fluid flow communication is prevented through said valve and an open position wherein fluid flow communication is permitted; and
   a syringe, said syringe having a needle-less tip which is adapted to engage said valve and actuate said valve between said closed and open positions for taking a sample of said liquid from said collection chamber.

2. The combination according to claim 1, wherein said valve further comprises a body having a distal opening and a proximal opening, said proximal opening being in communication with a first interior chamber and said distal opening being in communication with a second interior chamber.

3. The combination according to claim 2, wherein said first and second interior chambers are separated by an inner shoulder which defines an aperture.

4. The combination according to claim 3, wherein said valve further comprises a push rod having an elongated body which is slidably disposed inside said first and second interior chambers.

5. The combination according to claim 4, wherein said push rod defines a proximal portion, distal portion and middle portion.

6. The combination according to claim 5, wherein said valve further comprises an activation member for operating said valve between said open and closed positions.

7. The combination according to claim 1, wherein said valve further comprises an activation member for operating said valve between open and closed positions.

8. The combination according to claim 6, wherein said activation member is attached to said proximal end of said push rod.

9. The combination according to claim 5, wherein said middle portion forms a flange.

10. The combination according to claim 9, wherein a seal is provided adjacent said flange for sealing off said aperture to fluid flow communication when said valve is placed in the closed position.

11. The combination according to claim 10, wherein said valve further comprises at least one spring for applying a spring force that places said valve in said closed position.

12. The combination according to claim 2 wherein said body further includes a flange.

13. The combination according to claim 12, wherein said drainage device further comprises a retention portion formed adjacent said aperture, said retention portion being adapted to securely engage said flange of said valve within said aperture.

14. The combination according to claim 2, wherein said body further includes an insert securely engaged to said distal end of said body.

15. A method of withdrawing a sample from a drainage device comprising the steps of:
   a) providing a drainage device having a casing, said casing defining a collection chamber for the collection of liquid drained from a cavity of a patient, said casing further defining an aperture in communication with said collection chamber, said casing further including a sampling port having a valve securely disposed inside said aperture and in communication with said collection chamber, said valve being operable between a normally closed position wherein fluid flow communication is prevented through said valve and an open position wherein fluid flow communication is permitted through said valve;
   b) providing a syringe, said syringe having a needle-less tip;
   c) inserting said needle-less tip into said valve;
   d) actuating said valve with said needle-less tip such that said valve is placed in the open position;
   e) withdraw a sample of said liquid from said collection chamber through said valve; and
   f) disengage said needle-less tip from said valve.

16. The method according to claim 15, wherein said valve is a mechanical valve adapted to be actuated by said needle-less tip of said syringe.

17. The method according to claim 15, wherein said syringe is a luer tip syringe.

18. The method according to claim 15, wherein said syringe further includes a slidable plunger that a user actuates in order to withdraw said sample from said collection chamber and into said syringe.

19. The method according to claim 15, wherein said valve includes a hollow body having an activation member operatively associated with a push rod which places said valve between said open and closed positions.

20. The method according to claim 19, wherein said step of actuating said valve further includes engaging said activation member with said needle-less tip in order to place said valve between said open and closed positions by said push rod.

21. The method according to claim 15, wherein said valve includes a hollow body having a valve member operatively associated with a spring which places said valve between said open and closed positions.

22. The method according to claim 21, wherein said step of actuating said valve further includes engaging said needle-less tip to said sampling port and creating sufficient suction to place said valve member in said open position.

* * * * *